United States Patent [19]
Lipshitz et al.

[11] Patent Number: 6,007,579
[45] Date of Patent: Dec. 28, 1999

[54] INTRAOCULAR CARRYING MEMBER WITH ATTACHMENT FOR TELESCOPE

[75] Inventors: Isaac Lipshitz, Herzliva Pituach; Yosef Gross, Moshav Mazor; Gideon Dotan, Yehud; Eli Aharoni, Rishon lë Zion, all of Israel

[73] Assignee: Visioncare Ltd., Yehud, Israel

[21] Appl. No.: 09/007,380

[22] Filed: Jan. 15, 1998

[51] Int. Cl.$^6$ ..................................................... A61F 2/16
[52] U.S. Cl. .................................................................. 623/6
[58] Field of Search ....................................................... 623/6

[56] References Cited

U.S. PATENT DOCUMENTS

| | | |
|---|---|---|
| 4,074,368 | 2/1978 | Levy, Jr. et al. . |
| 4,172,297 | 10/1979 | Schlegel . |
| 4,451,938 | 6/1984 | Kelman ........................................ 623/6 |
| 4,759,761 | 7/1988 | Portnoy . |
| 4,892,543 | 1/1990 | Turley .......................................... 623/6 |
| 4,932,971 | 6/1990 | Kelman ........................................ 623/6 |
| 4,994,082 | 2/1991 | Richards et al. . |
| 5,222,981 | 6/1993 | Werblin . |
| 5,275,623 | 1/1994 | Sarfarazi . |
| 5,326,347 | 7/1994 | Cumming ..................................... 623/6 |
| 5,354,335 | 10/1994 | Lipshitz et al. . |
| 5,358,520 | 10/1994 | Patel ............................................. 623/6 |
| 5,391,202 | 2/1995 | Lipshitz et al. . |
| 5,628,798 | 5/1997 | Eggleston et al. . |
| 5,728,155 | 3/1998 | Anello et al. ................................ 623/6 |
| 5,814,103 | 9/1998 | Lipshitz et al. ............................. 623/6 |

FOREIGN PATENT DOCUMENTS

| | | |
|---|---|---|
| 0 194 390 A1 | 9/1986 | European Pat. Off. ................... 623/6 |
| 0 212 616 | 3/1987 | European Pat. Off. . |
| 36 26 869 A1 | 2/1988 | Germany .................................... 623/6 |
| 4403326 | 6/1995 | Germany . |
| WO 94/07435 | 4/1994 | WIPO . |

*Primary Examiner*—David H. Willse
*Attorney, Agent, or Firm*—Darby & Darby

[57] ABSTRACT

An intraocular lens implant including a carrying member, a telescope, and at least one mechanical fastener that fixedly attaches the telescope to the carrying member. Either the carrying member or the telescope may be integrally formed with the at least one mechanical fastener. For example, the carrying member may be formed with a female fastener which mates with a corresponding male fastener formed on the telescope. Alternatively, the carrying member may be formed with a male fastener which mates with a corresponding female fastener formed on the telescope.

4 Claims, 4 Drawing Sheets

INTRAOCULAR CARRYING MEMBER WITH ATTACHMENT FOR TELESCOPE

FIELD OF THE INVENTION

The present invention relates generally to intraocular lens (IOL) implants and particularly to an intraocular carrying member with mechanical attachments for telescopes.

BACKGROUND OF THE INVENTION

Intraocular inserts comprising telescopes are known. European Published Patent Application EP-A-212616 describes an intraocular lens that includes an anterior convex lens and a posterior concave lens. The contour of the lens can be selectively changed by varying the amount of fluid therein in order to change its refractive power. The lens is intended solely as a replacement for the natural lens of the eye.

U.S. Pat. No. 4,074,368 also describes an intraocular lens that includes an anterior convex lens and a posterior concave lens with high magnification proposed for the relief of conditions such as macular degeneration and diabetic retinopathy. The lens has many relatively low power lens surfaces arranged in a relatively long lens assembly which extends, when implanted, through almost the entire depth of the eye, from the pupil nearly to the retina. Implanting such a lens would necessitate major surgery. Moreover, the proposed lens does not provide a replacement for the natural lens for a wide field of view.

French Published Patent Application 2,666,735 describes an implant that includes a lens-shaped optical portion and a fastening assembly for securing the implant in the eye. The optical portion includes at least one closed internal cavity which contains a fluid or vacuum, forming a refraction chamber changing the optical properties of the lens.

Applicant/assignee's U.S. Pat. Nos. 5,354,335 and 5,391,202, the disclosures of which are incorporated herein by reference, describe intraocular inserts with a positive (converging) lens facing the anterior side of the eye and a negative (diverging) lens facing the posterior side, the two lenses forming a Galilean telescopic system. In U.S. Pat. No. 5,354,335, the lenses are assembled in a body member, the positive lens being generally flush with the anterior face of the body member. The negative lens may either be flush with the posterior face of the body member, or may project posteriorly therefrom. The body member anterior and/or posterior faces may be convex. In U.S. Pat. No. 5,391,202, the positive lens projects anteriorly from the anterior face of the body member which is preferably a soft lens constructed from a material such as a silicone.

In U.S. patent application Ser. No. 08/882,972, the disclosure of which is incorporated herein by reference, the present applicant/assignee discloses a further intraocular implant comprising a telescope body having an anterior end and a posterior end and including one or more windows sealed to the telescope body at the anterior end and/or the posterior end. There are at least two lenses disposed within the telescope body intermediate the anterior and posterior ends. The lenses may be a so-called reverse Galilean telescope, i.e., a negative lens faces the anterior side of the eye while a positive lens faces the posterior side of the eye. One of the features of the system is that the lenses are doublet lenses. The windows may be formed without optical power, or alternatively, may comprise a prism.

In U.S. patent application Ser. No. 08/882,973, the disclosure of which is incorporated herein by reference, the present applicant/assignee discloses yet another intraocular implant comprising a telescope (either Galilean or reverse Galilean) which extends through at least a portion of a lens capsule of the eye and forwardly thereof toward the anterior side of the eye, the telescope not penetrating the vitreous of the eye. The intraocular lens implant is supported within the lens capsule by loops, in the absence of a lens within the lens capsule. One of the features of the system is that the telescope may be tilted such that light from outside the eye is focused by the telescope on a low resolution but operative section of the retina. Other optional features of the system include one or more lenses having a graded index of refraction, holographic (diffusing) lenses, and/or doublet lenses which help prevent chromatic aberrations. The patent application also discloses a method for manufacturing an intraocular insert telescope employing laser fusing to join the lenses to the telescope body. Alternatively or additionally, the method employs glass particles having a low temperature melting point as a joining medium.

SUMMARY OF THE INVENTION

The present invention seeks to provide an improved telescopic lens system extending from an IOL. The present invention provides an intraocular carrying member with mechanical attachments for telescopes. In one embodiment of the present invention, the carrying member is constructed like a retaining ring for supporting a telescope. (It is noted that throughout the specification and claims the terms retaining ring and circlip are interchangeable.) The carrying member snaps onto the body of the telescope, thereby providing an inexpensive and quick method for constructing a telescoping intraocular insert. The finished assembly may be readily attached in an eye, typically in the capsular bag. Other mechanical attachments, such as threaded fasteners, snaps and studs, are also disclosed.

The present invention thus provides a novel method of constructing an intraocular implant with a telescope, either in the factory or in situ during implantation in the eye. It is noted that the "carrying member" of the present invention is not a lens, but rather any structure suitable for implantation in the eye and which is used to support the telescope in the eye. The carrying member is illustrated herein as having the general shape of a lens. However, it is appreciated that any other shape may be used and is in the scope of the present invention.

There is thus provided in accordance with a preferred embodiment of the present invention an intraocular lens implant including a carrying member, a telescope, and at least one mechanical fastener that fixedly attaches the telescope to the carrying member.

In accordance with a preferred embodiment of the present invention at least one of the carrying member and the telescope is integrally formed with the at least one mechanical fastener.

Further in accordance with a preferred embodiment of the present invention the carrying member is formed with a female fastener which mates with a corresponding male fastener formed on the telescope. Alternatively, the carrying member is formed with a male fastener which mates with a corresponding female fastener formed on the telescope. Preferably the fastener of the telescope is formed at an end of the telescope.

In accordance with a preferred embodiment of the present invention the carrying member includes a ring having a bore formed therethrough defining an inner diameter and an outer diameter, the ring being split at one point by a gap extending from the inner to the outer diameter, the ring being constructed of a material that is biocompatible for insertion into a human eye, the material having sufficient resiliency so that the ring can be sprung open from an initial configuration by widening the gap upon application of a force to the ring and the ring generally returns to the initial configuration upon removal of the force, and the telescope includes a body with a perimeter shaped to receive therearound the bore of the ring, wherein the ring is attached to the telescope body by springing open the ring with the force, passing the ring over the body and removing the force to allow the ring to fixedly grip the perimeter. Preferably the carrying member includes at least one haptic extending therefrom.

Further in accordance with a preferred embodiment of the present invention the ring has a pair of holes formed in a portion of the ring intermediate the inner and outer diameters and in propinquity to the gap, one hole being on one side of the gap and the other hole being on an opposite side of the gap. Preferably the perimeter is defined by an annular recess formed on the body. Additionally or alternatively, at least one annular ridge is formed on the telescope body.

In accordance with a preferred embodiment of the present invention the male fastener includes at least one stud and the female fastener is a groove formed by a first socket connected by a notch to a second socket, the notch being narrower than the sockets, wherein the at least one stud is fixedly inserted into the second socket by first inserting the at least one stud into the first socket and forcibly passing the at least one stud past the notch into the second socket.

Further in accordance with a preferred embodiment of the present invention the fasteners are threadably engageable with each other.

Still further in accordance with a preferred embodiment of the present invention the male fastener includes at least one protrusion and wherein the female fastener includes at least one tab, wherein rotation of the telescope with respect to the carrying member snugly and fixedly mates the at least one protrusion with the at least one corresponding tab.

In accordance with a preferred embodiment of the present invention the male fastener includes a flange and wherein the female fastener includes at least one elastic tongue, wherein the flange snaps together with the at least one tongue.

Further in accordance with a preferred embodiment of the present invention the at least one mechanical fastener is provided separately from the carrying member and the telescope. The telescope may include an end face which has a curvature to match a curvature of the carrying member. The telescope may include an anteriorly positioned positive lens and a posteriorly positioned negative lens. Alternatively, the telescope may include an anteriorly positioned negative lens and a posteriorly positioned positive lens.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
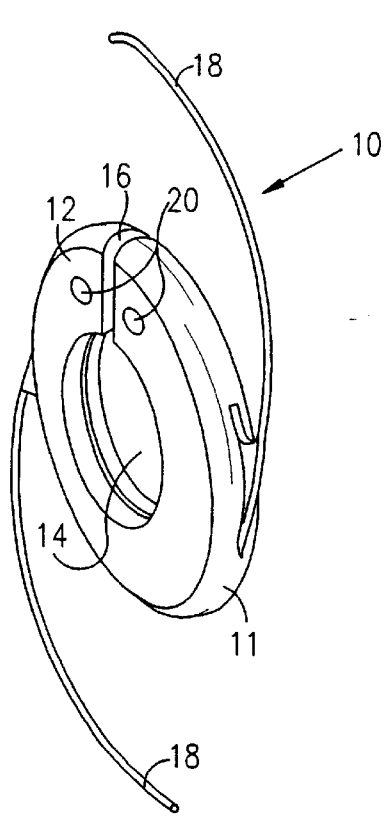
FIG. 1 is a simplified pictorial illustration of an intraocular carrying member implant shaped like a retaining ring, constructed and operative in accordance with a preferred embodiment of the present invention.

Reference is now made to FIG. 1 which illustrates an intraocular carrying member implant 10 constructed and operative in accordance with a preferred embodiment of the present invention.

Lens implant 10 includes a carrying member 11 shaped in the form of a ring 12 having a bore 14 formed therethrough defining an inner diameter and an outer diameter. Bore 14 is most preferably formed through the center of ring 12. Ring 12 is split at one point by a gap 16 extending from the inner to the outer diameter. Ring 12 is constructed of a material that is biocompatible for insertion into a human eye, which material having sufficient resiliency so that ring 12 acts like a circlip. In other words, ring 12 can be sprung open from an initial configuration by widening gap 16 upon application of a force to ring 12. Ring 12 generally returns to the initial configuration upon removal of the force. A suitable material for ring 12 is polymethylmethacrylate (PMMA), for example.

Ring 12 preferably includes one or more haptics 18 extending therefrom. A pair of holes 20 are formed in a portion of ring 12 intermediate the inner and outer diameters and in propinquity to gap 16. One hole 20 is on one side of gap 16 and the other hole 20 is on an opposite side of gap 16.

Figure 2:
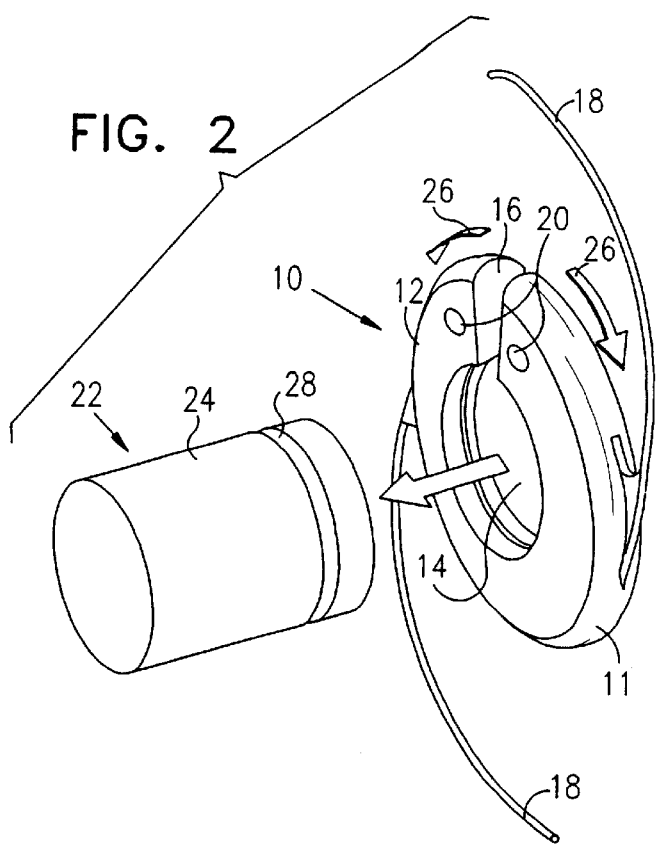
FIG. 2 is a simplified pictorial, exploded illustration of the intraocular carrying member implant of FIG. 1 before assembly on a telescope.
Figure 3:
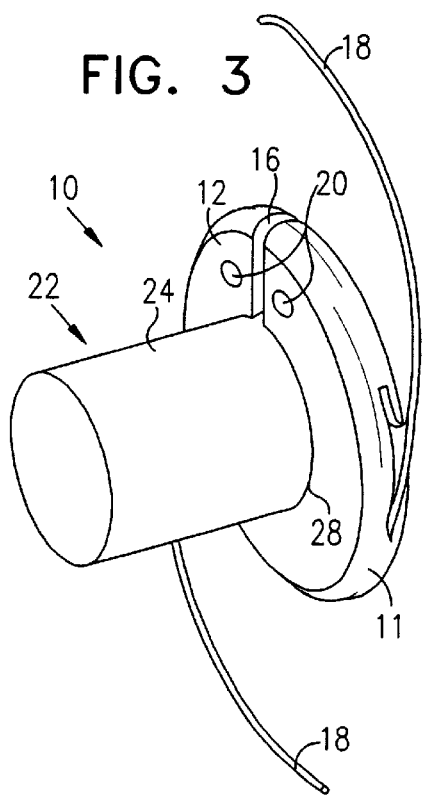
FIG. 3 is a simplified pictorial illustration of the intraocular carrying member implant of FIG. 1 assembled on the telescope in accordance with a preferred embodiment of the present invention.

Reference is now made to FIGS. 2 and 3 which illustrate assembling ring 12 on a telescope 22. Telescope 22 may be constructed in accordance with the teachings of applicant/assignee's U.S. Pat. Nos. 5,354,335 and 5,391,202, or U.S. patent applications Ser. No. 08/882,972 or 08/882,973. As described in these references, telescope 22 may be either Galilean (having an anteriorly positioned positive lens and a posteriorly positioned negative lens) or reverse Galilean (having an anteriorly positioned negative lens and a posteriorly positioned positive lens). Telescope 22 has a body 24 with a perimeter shaped to receive therearound bore 14. As seen in FIG. 2, ring 12 may be attached to telescope body 24 by springing open ring 12 with a force generally in the direction of arrows 26 so as to widen gap 16. As is known in the art of retaining rings, a circlip tool (not shown) with nose jaws may be inserted in holes 20 to apply the force to widen gap 16 Ring 12 may then be passed over telescope body 24, whereupon the force in the direction of arrows 26 is removed to allow ring 12 to fixedly grip the perimeter of telescope body 24, as shown in Fir. 3. An annular recess 28 may be formed on telescope body 24 for receiving therein ring 12.

Figure 4:
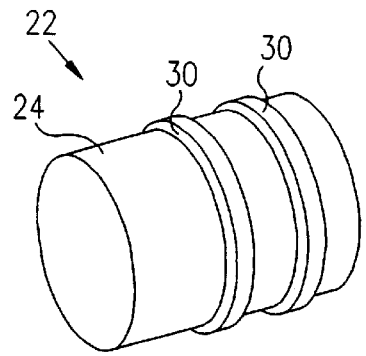
FIG. 4 is a simplified pictorial illustration of a telescope with annular ridges formed thereon, constructed and operative in accordance with a preferred embodiment of the present invention.

Alternatively, as seen in FIG. 4, one or more annular ridges 30 may be formed on telescope body 24 and ring 12 may be passed over telescope body 24 to firmly sit between ridges 30.

Figure 5:
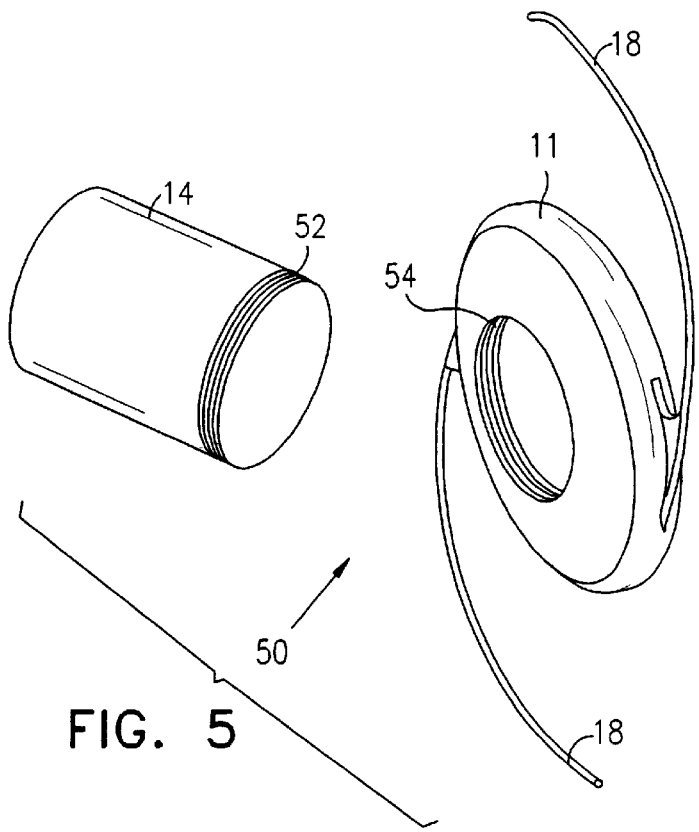
FIG. 5 is a simplified pictorial illustration of an intraocular lens implant constructed and operative in accordance with another preferred embodiment of the present invention, wherein the telescope is formed with a male thread which mates with a corresponding female thread formed on the carrying member.

Reference is now made to FIG. 5 which illustrates an intraocular lens implant 50 constructed and operative in accordance with another preferred embodiment of the present invention. In lens implant 50, telescope 14 is formed with a male thread 52 which mates with a corresponding female thread 54 formed on carrying member 11. Of course, alternatively, the female thread could be formed on the telescope and the male thread on the carrying member.

Figure 6:
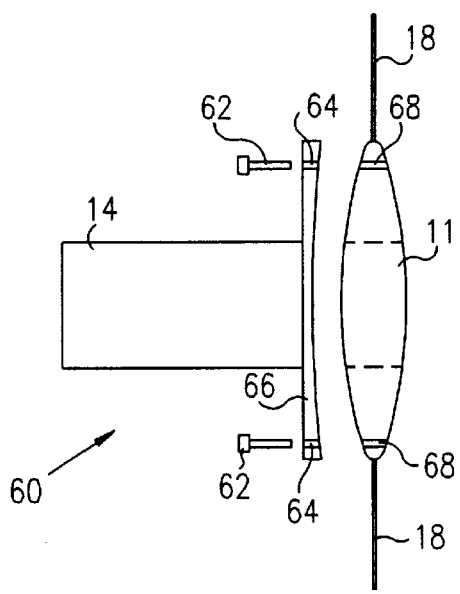
FIG. 6 is a simplified pictorial illustration of an intraocular lens implant constructed and operative in accordance with yet another preferred embodiment of the present invention, wherein the telescope is attached to the carrying member with separate mechanical fasteners.

Reference is now made to FIG. 6 which illustrates an intraocular lens implant 60 constructed and operative in accordance with yet another preferred embodiment of the present invention. In lens implant 60, telescope 14 is attached to carrying member 11 with separate mechanical fasteners 62, such as screws. For purposes of example only, fasteners 62 may fit through holes 64 formed in a flange 66 of telescope 14 and mate with threaded holes 68 formed in carrying member 11. It is seen in FIG. 6 that telescope 14 may include an end face which has a curvature (e.g., concavity) to match a curvature of carrying member 11 (e.g., convexity). This feature, of course, may be provided in any of the other intraocular lens implants of the present invention.

Figure 7:
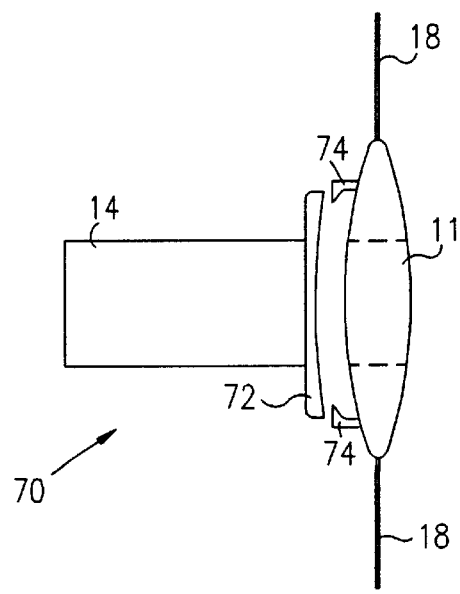
FIG. 7 is a simplified pictorial illustration of an intraocular lens implant constructed and operative in accordance with still another preferred embodiment of the present invention, wherein the telescope is formed with a flange which snaps together with elastic tongues formed on the carrying member.

Reference is now made to FIG. 7 which illustrates an intraocular lens implant 70 constructed and operative in accordance with still another preferred embodiment of the present invention. In lens implant 70, telescope 14 is formed with a flange 72 which snaps together with one or more elastic tongues 74 formed on carrying member 11. Of course, alternatively, the tongues could be formed on the telescope and the flange on the carrying member.

Figure 8:
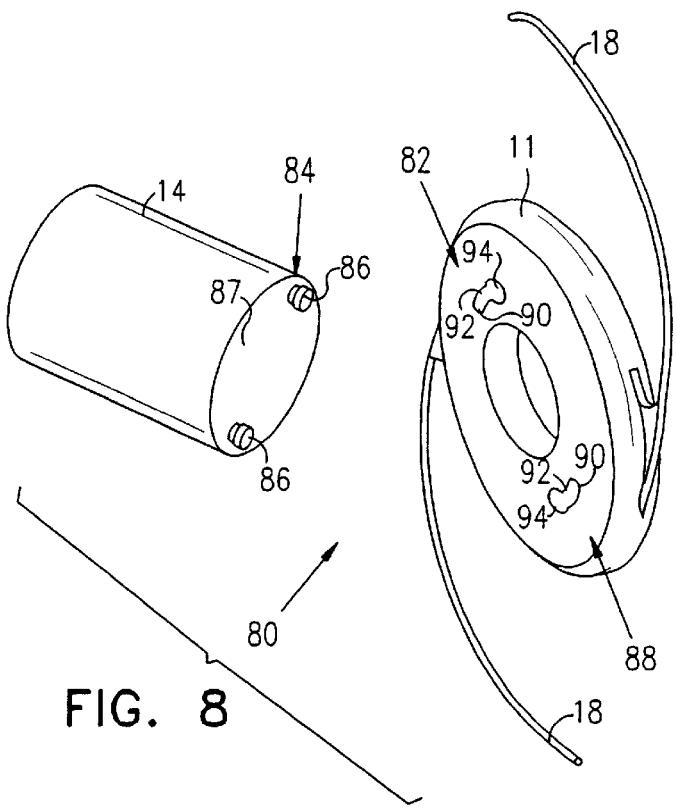
FIG. 8 is a simplified pictorial illustration of an intraocular lens implant constructed and operative in accordance with another preferred embodiment of the present invention, wherein the telescope has studs which mate with grooves in the carrying member.

Reference is now made to FIG. 8 which illustrates an intraocular lens implant 80 constructed and operative in accordance with another preferred embodiment of the present invention. In lens implant 80, carrying member 11 is formed with one or more female fasteners 82 and telescope 14 is formed with one or more corresponding male fasteners 84.

Male fastener 84 preferably includes one or more studs 86 protruding from an end 87 of telescope 14, and female fastener 82 includes one or more grooves 88 corresponding to studs 86. Each groove 88 is preferably formed by a first socket 90 connected by a notch 92 to a second socket 94. Notch 92 is preferably narrower than sockets 90 and 94 so that each stud 86 may be inserted into first socket 90, and then fixedly seated in second socket 94 by turning telescope 14 so as to forcibly pass stud 86 past notch 92. The outer dimension of stud 86, in the case of a cylindrical stud the diameter, and the material of stud are selected so that stud 86 is preferably slightly compressed as it passes through notch 92. A suitable material for stud 86, as well as for the rest of lens implant 80, is polymethylmethacrylate (PEMA), for example.

Figure 9:
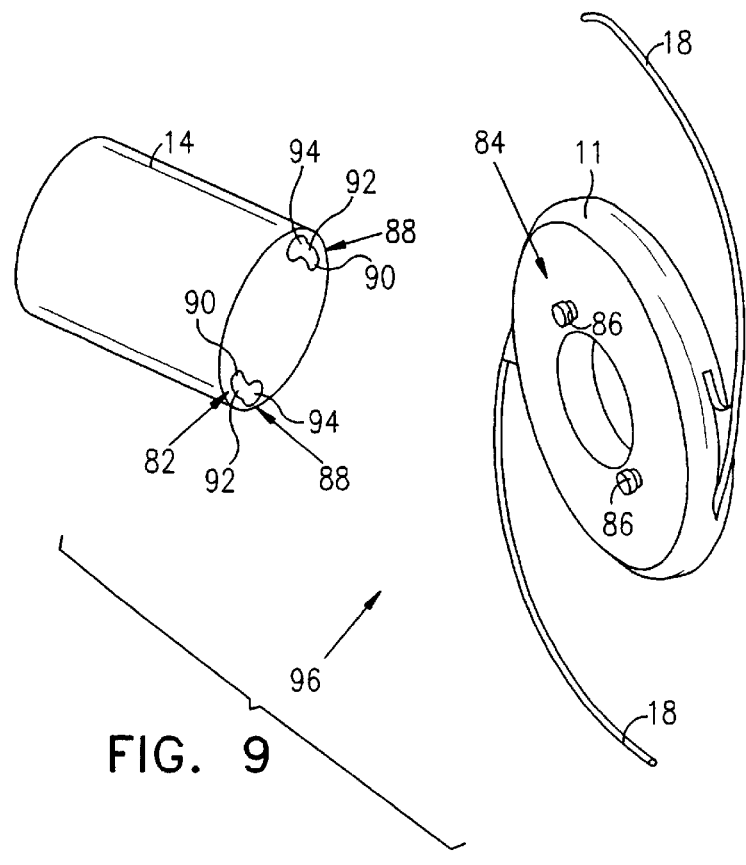
FIG. 9 is a simplified pictorial illustration of an intraocular lens implant constructed and operative in accordance with yet another preferred embodiment of the present; invention, wherein the carrying member has studs which mate with grooves in the telescope.

Reference is now made to FIG. 9 which illustrates an intraocular lens implant 96 constructed and operative in accordance with still another preferred embodiment of the present invention. Lens implant 96 is basically the same as lens implant 80 except that carrying member 11 is formed with male fasteners 84 which mate with the corresponding female fasteners 82 formed on telescope 14.

Figure 10:
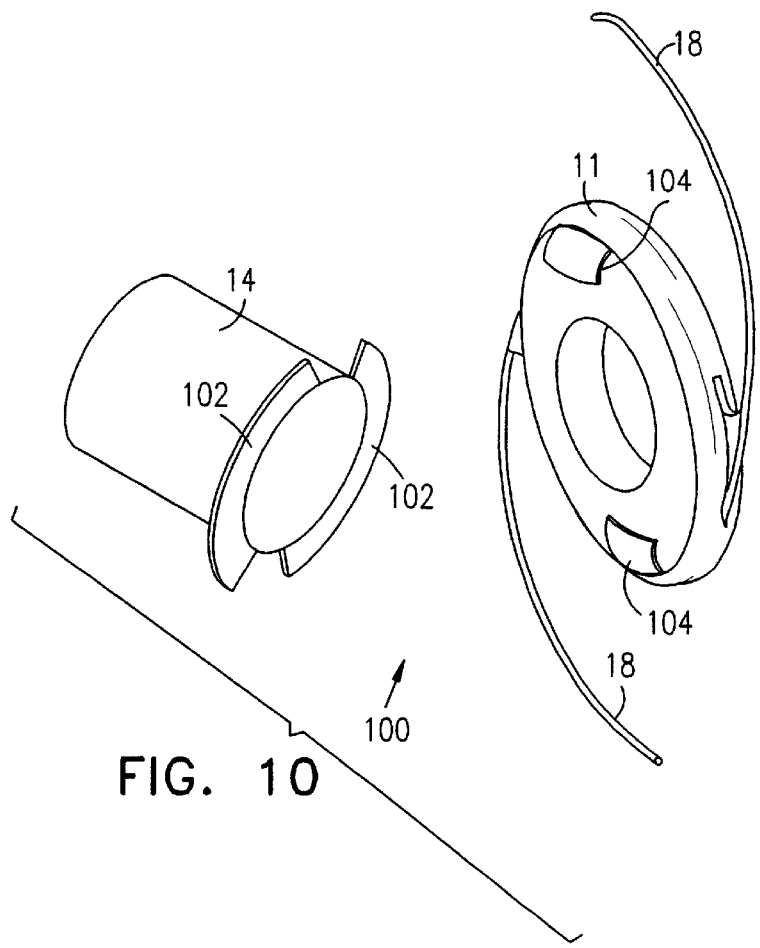
FIG. 10 is a simplified pictorial illustration of an intraocular lens implant constructed and operative in accordance with still another preferred embodiment of the present invention, wherein the telescope has annular protrusions which mate with tabs formed on the carrying member.

Reference is now made to FIG. 10 which illustrates an intraocular lens implant 100 constructed and operative in accordance with yet another preferred embodiment of the present invention. In lens implant 100, telescope 14 is formed with one or more annular protrusions 102 which snugly and fixedly mate with one or more tabs 104 formed on carrying member 11. Protrusions 102, preferably formed at an end of telescope 14, are forcibly slid under tabs 104 by suitably rotating telescope 14 and carrying member 11 with respect to each other. Protrusions 102 thus act as male fasteners and tabs 104 act as female fasteners. Of course, alternatively, the tabs could be formed on the telescope and the protrusions on the carrying member.

Figure 11:
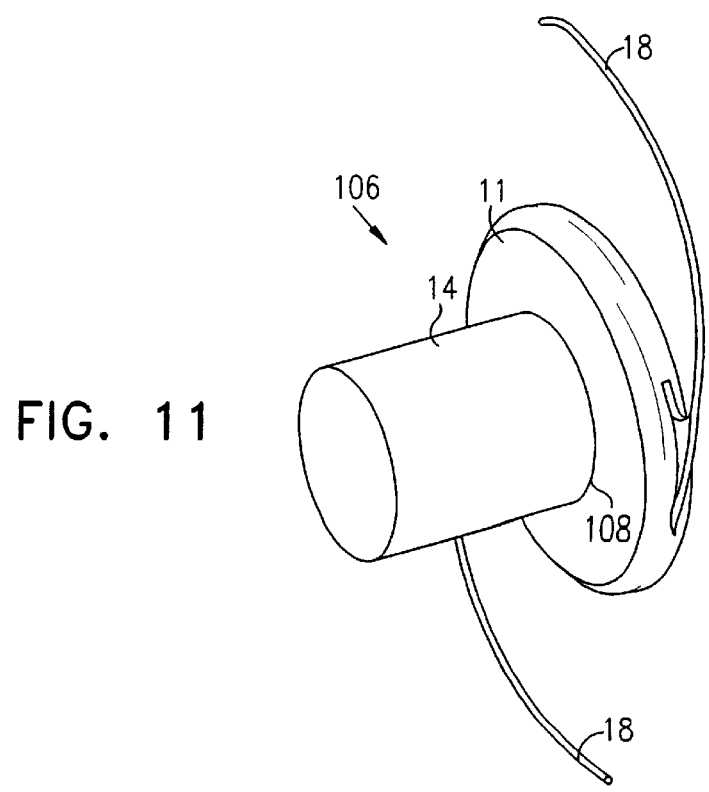
FIG. 11 is a simplified pictorial illustration of an intraocular lens implant constructed and operative in accordance with another preferred embodiment of the present invention, wherein the telescope is bonded to the carrying member.

Reference is now made to FIG. 11 which illustrates an intraocular lens implant 106 constructed and operative in accordance with still another preferred embodiment of the present invention. In lens implant 106, telescope 14 is bonded to carrying member 11, such as by means of a biocompatible adhesive 108.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An intraocular lens implant comprising a carrying member, a telescope, and at least one mechanical fastener that fixedly attaches said telescope to said carrying member, wherein said carrying member comprises:

a ring having a bore formed therethrough defining an inner diameter and an outer diameter, said ring being split at one point by a gap extending from the inner to the outer diameter, said ring being constructed of a material that is biocompatible for insertion into a human eye, said material having sufficient resiliency so that said ring can be sprung open from an initial configuration by widening said gap upon application of a force to said ring and said ring generally returns to said initial configuration upon removal of said force; and said telescope comprises a body with a perimeter shaped to receive therearound said bore of said ring, wherein said ring is attached to said telescope body by springing open said ring with said force, passing said ring over said body and removing said force to allow said ring to fixedly grip said perimeter.

2. The implant according to claim 1 wherein said ring has a pair of holes formed in a portion of said ring intermediate the inner and outer diameters and in propinquity to said gap, one hole being on one side of said gap and the other hole being on an opposite side of said gap.

3. The implant according to claim 2 and wherein said perimeter is defined by an annular recess formed on said body.

4. The implant according to claim 2 and wherein at least one annular ridge is formed on said telescope body.

* * * * *